US00PP26002P2

(12) United States Plant Patent
Boereboom

(10) Patent No.: US PP26,002 P2
(45) Date of Patent: Oct. 20, 2015

(54) ***NANDINA* PLANT NAMED 'SUNSET BOULEVARD'**

(50) Latin Name: *Nandina domestica*
Varietal Denomination: Sunset Boulevard

(71) Applicant: André Boereboom, Eindhoven (NL)

(72) Inventor: André Boereboom, Eindhoven (NL)

( * ) Notice: Subject to any disclaimer, the term of this patent is extended or adjusted under 35 U.S.C. 154(b) by 102 days.

(21) Appl. No.: 13/999,157

(22) Filed: Jan. 21, 2014

(51) Int. Cl.
*A01H 5/00* (2006.01)

(52) U.S. Cl.
USPC ..... Plt./235

(58) Field of Classification Search
USPC ..... Plt./235
See application file for complete search history.

*Primary Examiner* — Susan McCormick Ewoldt
(74) *Attorney, Agent, or Firm* — Barbara Campbell; Bethany R. Roahrig; Cochran Freund & Young, LLC

(57) ABSTRACT

A new *Nandina domestica* plant particularly distinguished by having orange-brown to light-orange immature foliage and light-green mature foliage, dense, relatively narrow foliage, a compact plant shape, and densely branched, is disclosed.

3 Drawing Sheets

Genus and species: *Nandina domestica.*
Variety denomination: 'Sunset Boulevard'.

BACKGROUND OF THE NEW PLANT

The present invention comprises a new and distinct variety of *Nandina*, botanically known as *Nandina domestica* and hereinafter referred to by the variety name 'Sunset Boulevard'. 'Sunset Boulevard' was discovered as a chance seedling in group of *Nandina domestica* plants in May 2010 in Eindhoven, The Netherlands. The female and male parents of the 'Sunset Boulevard' are un-named *Nandina domestica* (unpatented) plants.

In October 2012, 'Sunset Boulevard' was first asexually propagated by tissue culture. 'Sunset Boulevard' was found to reproduce true to type in successive generations of asexual propagation via tissue culture in Eindhoven, The Netherlands.

SUMMARY

The following are the most outstanding and distinguishing characteristics of this new variety when grown under normal horticultural practices in Eindhoven, The Netherlands.

1. Orange-brown to light-orange foliage immature foliage and green mature foliage;
2. Dense, relatively narrow foliage;
3. A compact plant shape; and
4. Densely branched.

DESCRIPTION OF THE PHOTOGRAPHS

This new *Nandina* plant is illustrated by the accompanying photographs which show a whole plant view and close-up views of the foliage and stems. The photographs are of a plant approximately four-years-old grown in a greenhouse in Eindhoven, The Netherlands in September 2013. The colors shown are as true as can be reasonably obtained by conventional photographic procedures.

DESCRIPTION OF THE NEW VARIETY

Figure 1:
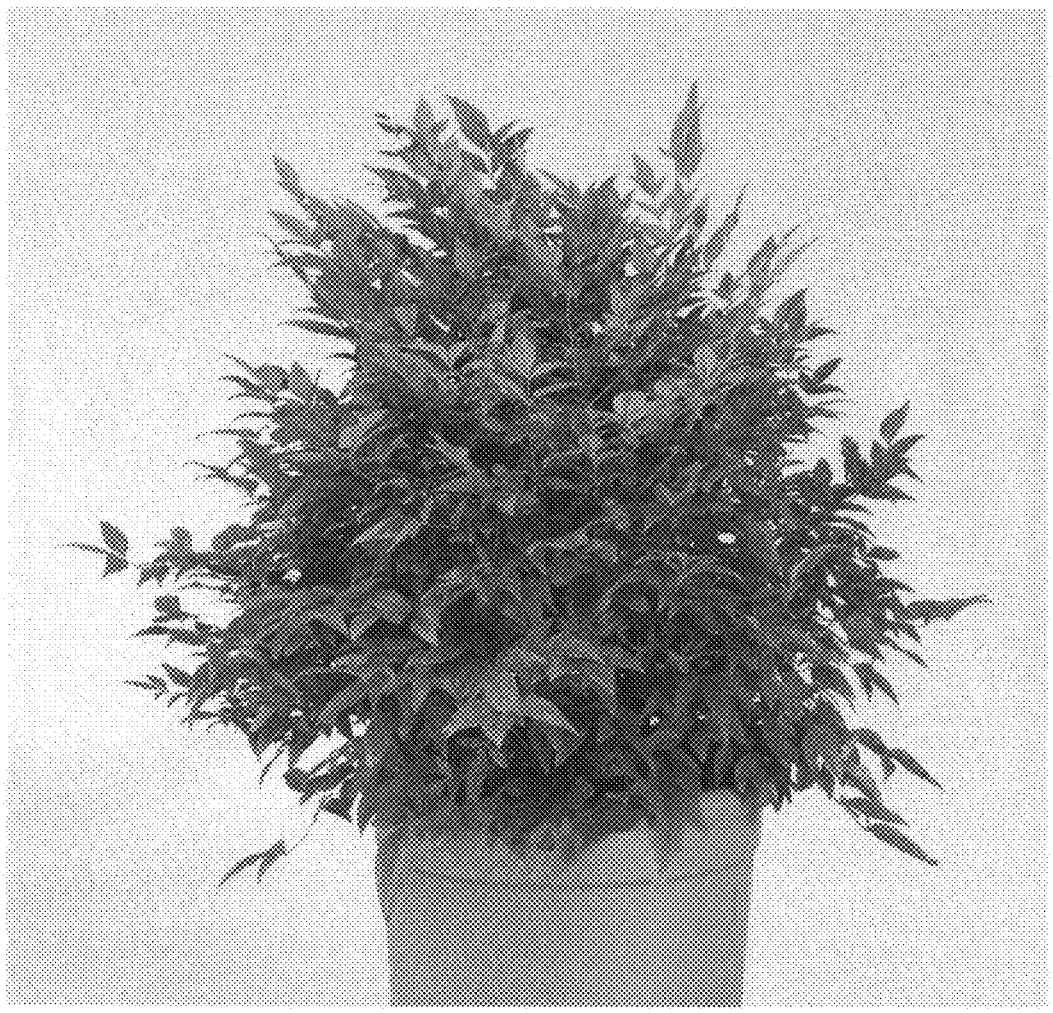
FIG. 1 shows an overall view of the whole plant in a container.
Figure 2:
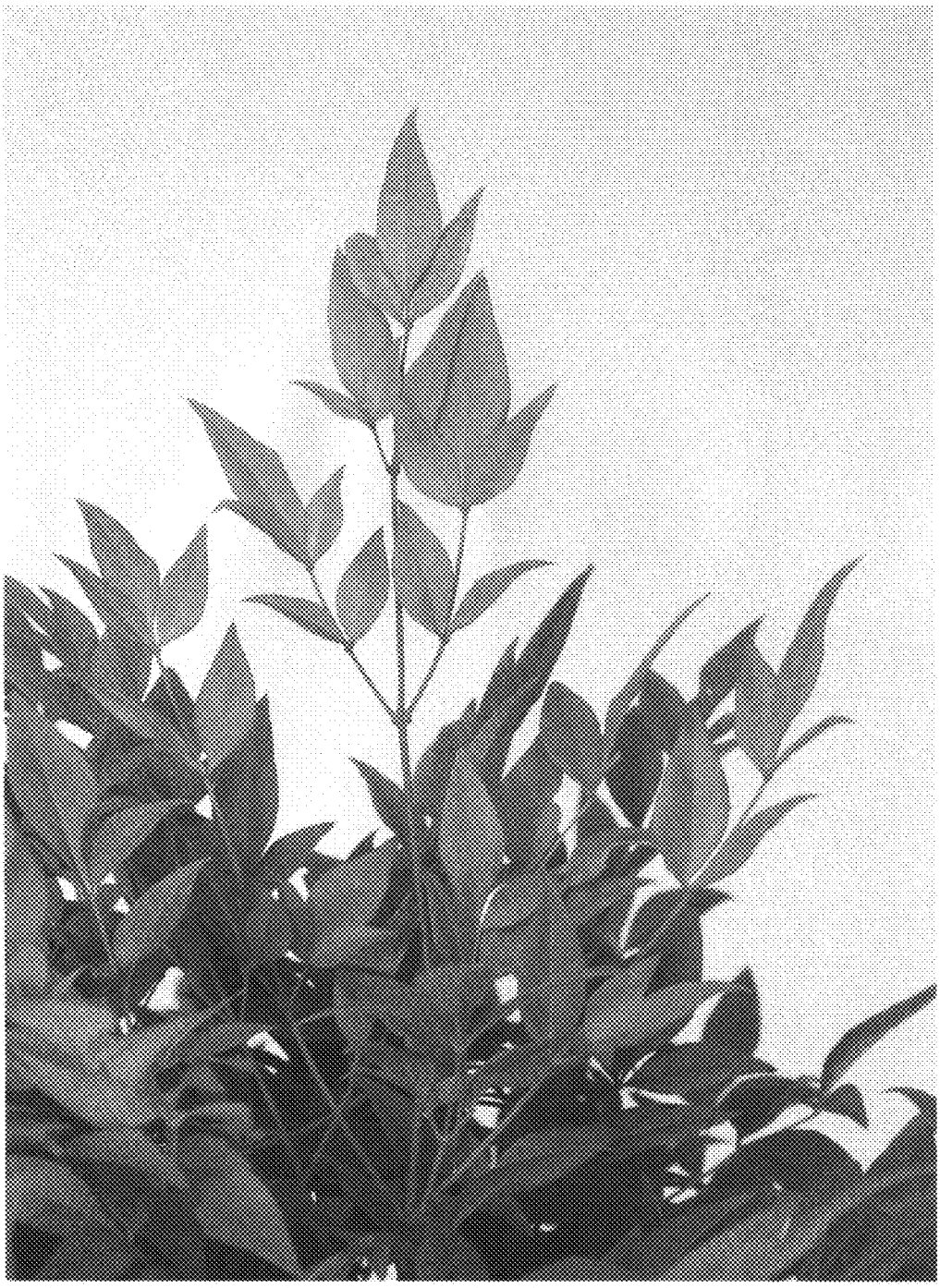
FIG. 2 shows a close-up of the immature foliage of the plant.
Figure 3:
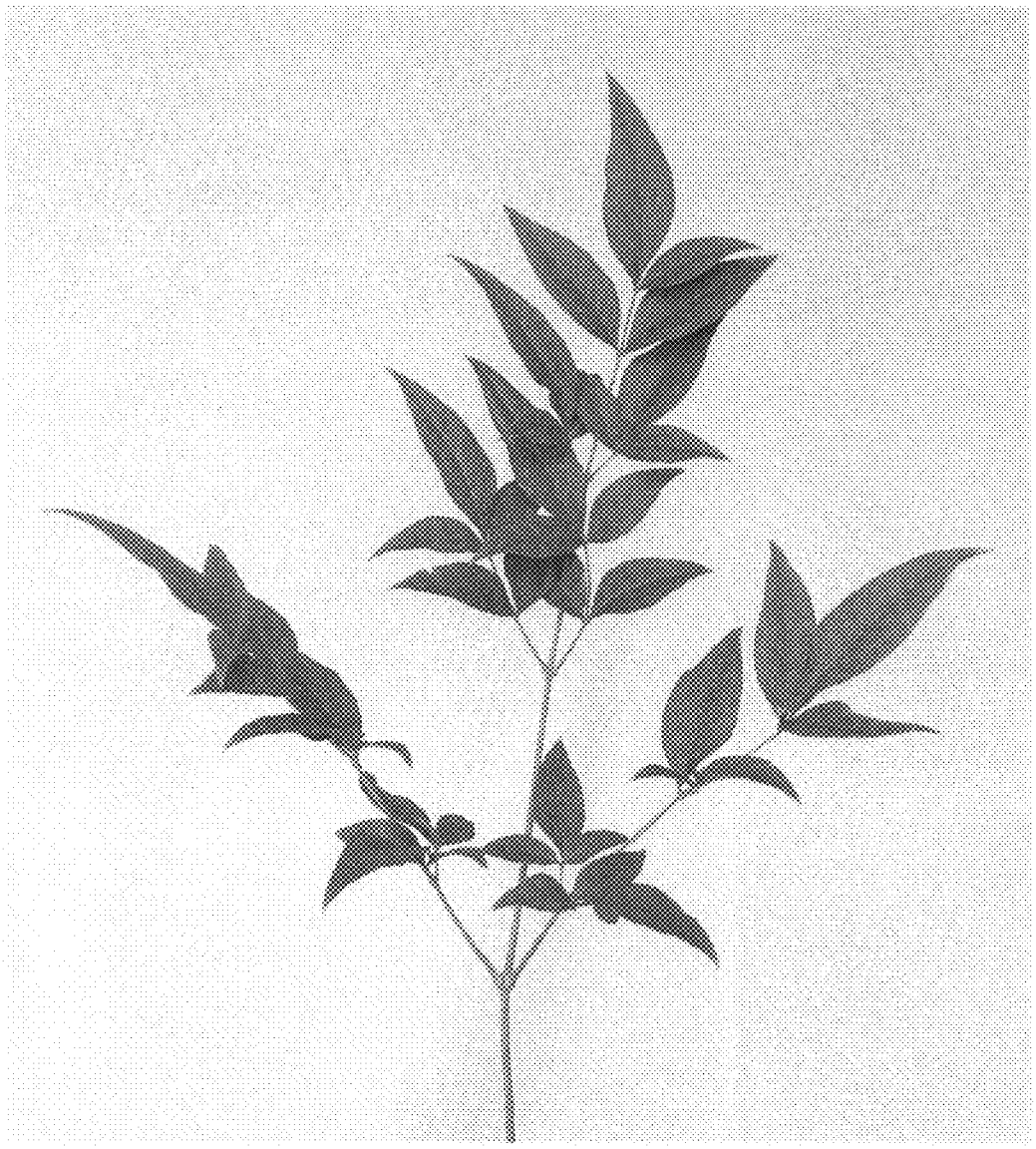
FIG. 3 shows a close-up of the mature foliage of the plant.

The following detailed descriptions set forth the distinctive characteristics of 'Sunset Boulevard'. The data which define these characteristics were collected from asexual reproductions carried out in Eindhoven, The Netherlands. Data was collected on four-year-old plants grown in a greenhouse in Eindhoven, The Netherlands in September 2013 where the average day temperatures were approximately 18° C. to 32° C. and where the average night temperatures were approximately 6° C. to 20° C. Color references are to The R.H.S. Colour Chart of The Royal Horticultural Society of London (R.H.S.), 5$^{th}$ edition (2007).

Classification:
- *Family.*—Berberidaceae.
- *Species.*—*Nandina domestica.*
- *Variety.*—'Sunset Boulevard'.

Plant:
- *Type.*—Perennial, evergreen shrub.
- *Growth rate.*—Moderately slow; approximately 15.0 cm per season.
- *Plant vigor.*—Moderate.
- *Plant shape.*—Broad oblong.
- *Growth habit.*—Broad upright.
- *Plant height.*—Approximately 47.1 cm.
- *Plant spread.*—Approximately 53.8 cm.
- *Time to produce a mature plant.*—Approximately two years from propagation.
- *Appropriate container systems.*—1.5 liter and larger containers.
- *Hardiness.*—USDA zones 6b to 10.
- *High temperature tolerance.*—At least tolerant up to 35° C.
- *Low temperature tolerance.*—At least hardy to USDA zone 6b.

Stems:

*General*.—Free-branching; has mainly basal stems and very few lateral branches.

*Main stem*.—Length: Average is 17.9 cm. Diameter: Average is 0.3 cm.

*Lateral stem*.—Length: Average is 6.2 cm. Diameter: Average is 0.25 cm.

*Internode length*.—Average is 1.1 cm but ranges from 0.2 cm to 2.1 cm.

*Appearance*.—Rounded, glossy.

*Aspect*.—Nearly vertical.

*Strength*.—Very strong.

*Color*.—RHS 151B to RHS 151C (Yellow-green); older stems are RHS N199B (Grey-brown).

*Texture*.—Glabrous; pubescence absent.

Leaves:

*Arrangement*.—Alternate, compound, and tri-pinnate; composed of an average of 32 leaflets or ranging from between 21 and 53 leaflets.

*Quantity*.—17 per lateral branch.

*Shape*.—Ovate to broad ovate.

*Length*.—Average is 17.9 cm.

*Width*.—Average is 14.6 cm.

*Pubescence*.—Absent.

*Rachis* (*main petiole*): Length: Average is 27.3 cm. Diameter: Average is 0.2 cm. Color: Upper surface is RHS N137A (Green) and lower surface is RHS 138A (Green).

*Durability of foliage to stresses*.—Moderate to high.

*Leaflets*.—Quantity per leaf: Average is 32, ranges between 21 and 53. Shape: Ovate. Apex: Acuminate. Base: Acuminate. Margin: Entire. Pubescence: Absent. Length: Average is 3.6 cm. Length of top leaflet: Average is 4.8 cm. Width: Average is 1.5 cm. Width of top leaflet: Average is 1.6 cm. Texture and appearance: Glabrous; upper surface is slightly glossy, while lower surface is matte. Color, immature: Upper surface: RHS 173A (Greyed-orange). Lower surface: RHS 176A (Greyed-orange) to RHS 178B (Greyed-red). Color, mature: Upper surface: Between RHS N137A (Green) and RHS 139A (Green). Lower surface: RHS 138A (Green) to RHS 138B (Green). Venation pattern: Pinnate. Venation color: Upper surface: Between RHS N137A (Green) and RHS 139A (Green). Lower surface: RHS 146A (Yellow-green) to RHS 146B (Yellow-green). Petiole length: Average is 9.0 mm. Petiole diameter: Average is 0.75 mm. Petiole color: Upper surface is RHS N137A (Green) and lower surface is RHS 138A (Green).

Flowers: None observed to date.

Reproductive organs: None observed to date.

Fruit and seed set: None observed to date.

Disease and pest resistance: Similar to other *Nandina domestica* varieties, however, somewhat susceptible to powdery mildew.

COMPARISON WITH PARENTAL LINES AND KNOWN VARIETIES

'Sunset Boulevard' is distinguished from its parents as described in Table 1.

TABLE 1

| Characteristic | 'Sunset Boulevard' | Un-named Female Parent | Un-named Male Parent |
|---|---|---|---|
| Immature leaf color | Orange-brown to light-orange | Bronze-green | Bronze-green |
| Foliage density | Dense | Less dense than 'Sunset Boulevard' | Less dense than 'Sunset Boulevard' |
| Branching | Dense | Less dense than 'Sunset Boulevard' | Less dense than 'Sunset Boulevard' |

'Sunset Boulevard' can be compared to the commercial *Nandina* plant varieties 'Gulf Stream' (U.S. Plant Pat. No. 5,656) and 'Seika' (U.S. Plant Pat. No. 21,891). Differences between the two varieties are described in Table 2.

TABLE 2

| Characteristic | 'Sunset Boulevard' | 'Gulf Stream' | 'Seika' |
|---|---|---|---|
| Immature leaf color | Orange-brown to light-orange | Red | Dark red |
| Mature leaf color | Green | Dark green | Dark green |
| Branching | Dense | Less dense than 'Sunset Boulevard' | Less dense than 'Sunset Boulevard' |

I claim:

1. A new and distinct variety of *Nandina* plant named 'Sunset Boulevard' as illustrated and described herein.

* * * * *